(12) United States Patent
Cheon et al.

(10) Patent No.: US 11,083,476 B2
(45) Date of Patent: Aug. 10, 2021

(54) UROLITHIASIS REMOVING DEVICE AND METHOD

(71) Applicants:EASYENDO SURGICAL, INC., Daejeon (KR); KOREA ADVANCED INSTITUTE OF SCIENCE AND TECHNOLOGY, Daejeon (KR)

(72) Inventors: Byung Sik Cheon, Daejeon (KR); Dong Soo Kwon, Daejeon (KR); Deok Gyoon Chung, Daejeon (KR)

(73) Assignees: EASYENDO SURGICAL, INC., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 17/030,369

(22) Filed: Sep. 23, 2020

(65) Prior Publication Data

US 2021/0007758 A1   Jan. 14, 2021

Related U.S. Application Data

(63) Continuation of application No. PCT/KR2019/004455, filed on Apr. 12, 2019.

(30) Foreign Application Priority Data

Apr. 12, 2018  (KR) .................. 10-2018-0042794
Apr. 12, 2019  (KR) .................. 10-2019-0043038

(51) Int. Cl.
*A61B 17/221*  (2006.01)
*A61B 90/00*  (2016.01)
(Continued)

(52) U.S. Cl.
CPC ........ *A61B 17/221* (2013.01); *A61B 1/00045* (2013.01); *A61B 1/0052* (2013.01);
(Continued)

(58) Field of Classification Search
CPC ............ A61B 17/221; A61B 17/32056; A61B 2017/2212; A61B 2017/2215;
(Continued)

(56) References Cited

U.S. PATENT DOCUMENTS

2009/0082780 A1\* 3/2009 Lu ..................... A61B 17/221
606/127
2014/0194737 A1  7/2014 Bailey et al.
(Continued)

FOREIGN PATENT DOCUMENTS

KR  20170102118  9/2017
KR  20170107618  9/2017

OTHER PUBLICATIONS

"International Search Report (Form PCT/ISA/210) of PCT/JP2019/004455," dated Jul. 15, 2019, with English translation thereof, pp. 1-4.

*Primary Examiner* — Wade Miles
*Assistant Examiner* — Kankindi Rwego
(74) *Attorney, Agent, or Firm* — JCIPRNET (57) ABSTRACT

A urolithiasis removing device according to one embodiment can comprise: an insertion tube; a guide which is inserted into the insertion tube and which is relatively movable with respect to the insertion tube; a wire which is inserted into the guide and which is relatively movable with respect to the guide; a basket positioned in front of the wire and capable of holding urolithiasis; and a control unit for determining the size of the urolithiasis on the basis of the relative movement of the guide with respect to the insertion tube or the relative movement of the wire with respect to the guide.

7 Claims, 5 Drawing Sheets

(51) Int. Cl.
  *A61B 1/00* (2006.01)
  *A61B 1/005* (2006.01)
  *A61B 1/307* (2006.01)
  *A61B 17/22* (2006.01)
  *A61B 17/00* (2006.01)

(52) U.S. Cl.
  CPC ...... *A61B 1/00085* (2013.01); *A61B 1/00108* (2013.01); *A61B 1/00142* (2013.01); *A61B 1/00147* (2013.01); *A61B 1/00154* (2013.01); *A61B 1/307* (2013.01); *A61B 90/06* (2016.02); *A61B 90/36* (2016.02); *A61B 2017/0034* (2013.01); *A61B 2017/00212* (2013.01); *A61B 2017/2215* (2013.01); *A61B 2017/22038* (2013.01); *A61B 2017/22084* (2013.01); *A61B 2090/061* (2016.02)

(58) Field of Classification Search
  CPC ............ A61B 2017/2217; A61B 34/25; A61B 2034/252; A61B 2034/254; A61B 2034/256; A61B 2034/258; A61B 1/0008; A61B 1/00085; A61B 1/00087; A61B 90/06; A61B 90/36; A61B 2090/061; A61B 2090/064; A61B 2017/22038; A61B 2017/22084
  USPC ....................................................... 606/127
  See application file for complete search history.

(56) References Cited

U.S. PATENT DOCUMENTS

| | | | |
|---|---|---|---|
| 2015/0327878 A1* | 11/2015 | Chu | A61B 17/221 606/127 |
| 2015/0366571 A1 | 12/2015 | Navve et al. | |
| 2016/0256179 A1 | 9/2016 | Walish et al. | |
| 2016/0374702 A1* | 12/2016 | St. George | A61B 90/03 606/127 |
| 2017/0020541 A1* | 1/2017 | Mahajan | A61B 17/221 |

\* cited by examiner

UROLITHIASIS REMOVING DEVICE AND METHOD

CROSS-REFERENCE TO RELATED APPLICATION

This is a continuation of International Application No. PCT/KR2019/004455, filed on Apr. 12, 2019, which claims the priority benefits of Korea Application No. 10-2018-0042794, filed on Apr. 12, 2018, and Korea Application No. 10-2019-0043038, filed on Apr. 12, 2019. The entirety of each of the above-mentioned patent applications is hereby incorporated by reference herein and made a part of this specification.

TECHNICAL FIELD

Example embodiments relate to a urolithiasis removing device and method.

BACKGROUND ART

A surgery is a medical procedure of treating a disease by cutting, incising, or applying a manipulation to the skin, moles, or other tissues using a medical machine. A laparotomy, in particular, which incises and opens the skin of a surgical site and treats, restores or reconstructs, or removes an organ in an abdominal cavity has some issues such as bleeding, side effects, pains, and/or scars of a patient. Thus, in recent years, a surgery using a robot has been receiving attention as an alternative.

A surgical robot may include a master device which generates and transmits a required signal in response to a manipulation of a surgeon, and a slave device which receives the signal from the master device and applies a manipulation required for a surgery directly to a patient. The master device and the slave device may be provided in an integral form, or configured as separate devices to be disposed at an operating room. Also, the master device and the slave device may be disposed apart from each other. In such a case, the surgeon may operate the slave device disposed at a distant location through the master device. In addition, a single master device may selectively interwork with one of multiple slave devices.

A urolithiasis refers to a stone in a body that is produced when a biogenic substance is solidified with an organic or inorganic matter, and may clog a biliary duct or a ureter. Thus, when a stone large enough to be of a dangerous size is found, it needs to be removed. A stone may be crushed by a crushing device or a lithotriptor, for example, a laser, and then collected by a basket and removed to outside. A surgical device for removing a stone may operate as the slave device.

A stone may be positioned deep inside a body, and thus it may not be easy to measure its size. When a stone grows to be large, it may damage an inner wall of a ureter while moving, and in severe cases, it may cut the ureter. The damaged inner wall of the ureter may cause an acute kidney infection, and the cut ureter may cause peritonitis. To prevent these, the size of a stone needs to be measured.

DISCLOSURE OF INVENTION

Technical Goals

An aspect provides a urolithiasis removing device and method that measures the size of a urolithiasis or a stone based on a movement distance of a basket.

Technical Solutions

According to an example embodiment, there is provided a urolithiasis removing device including an insertion tube, a guide configured to be inserted into an inner side of the insertion tube and relatively movable with respect to the insertion tube, a wire configured to be inserted into an inner side of the guide and relatively movable with respect to the guide, a basket disposed in front of the wire and configured to hold a stone, and a controller configured to determine a size of the stone based on a relative movement of the guide with respect to the insertion tube or a relative movement of the wire with respect to the guide.

The controller may determine the size of the stone based on a relative position of the wire with respect to the guide in a state in which the basket holding the stone is caught on a front end of the guide.

The urolithiasis removing device may further include a distance measurer disposed in the wire and configured to measure a relative movement distance of the wire with respect to the guide. The controller may determine the relative position of the wire with respect to the guide based on a distance detected by the distance measurer.

The distance measurer may be provided at a rear end of the wire and configured to measure a distance from the rear end of the wire to the guide.

The controller may determine the size of the stone based on a relative position of the wire with respect to the insertion tube in a state in which the basket holding the stone is caught on a front end of the insertion tube.

The urolithiasis removing device may further include a distance measurer disposed in the wire and configured to measure a relative movement distance of the wire with respect to the guide. The controller may determine the relative position of the wire with respect to the insertion tube based on a distance detected by the distance measurer.

The urolithiasis removing device may further include a sheath configured to surround the insertion tube. The insertion tube may be relatively movable with respect to the sheath.

The urolithiasis removing device may further include an impact detector provided in the sheath and configured to detect an impact applied to the sheath.

The urolithiasis removing device may further include a display configured to display information associated with the size of the stone and information as to whether an impact is detected by the impact detector.

According to another example embodiment, there is provided a urolithiasis removing device including a sheath, an insertion tube configured to be inserted into an inner side of the sheath and relatively movable with respect to the sheath, a guide configured to be inserted into an inner side of the insertion tube and relatively movable with respect to the insertion tube, a wire configured to be inserted into an inner side of the guide and relatively movable with respect to the guide, a basket disposed in front of the wire and configured to hold a stone, and a controller configured to determine a size of the stone based on a relative movement of the guide with respect to the insertion tube or a relative movement of the wire with respect to the guide.

The urolithiasis removing device may further include a distance measurer disposed in the wire and configured to measure a relative movement distance of the wire with respect to the guide, and an impact detector provided in the sheath and configured to detect an impact applied to the sheath.

The controller may determine the size of the stone based on a relative position of the wire with respect to the guide in a state in which the basket holding the stone is caught on a front end of the guide.

Advantageous Effects

According to an example embodiment described herein, a urolithiasis removing device and method may measure a position of a urolithiasis or a stone in an area near the position of the stone, for example, an area around renal pelvis, without a need for a user to take the stone out of a body.

According to an example embodiment described herein, a urolithiasis removing device and method may identify only a stone having a diameter less than an inner diameter of a sheath and selectively remove the stone, and detect a collision between the sheath and a basket immediately when the collision occurs. In addition, even though a diameter of a stone is greater than the inner diameter of the sheath, the urolithiasis removing device and method may enable a user to select whether to remove the stone based on a type of the stone.

BRIEF DESCRIPTION OF DRAWINGS

These and/or other aspects, features, and advantages of the present disclosure will become apparent and more readily appreciated from the following description of example embodiments, taken in conjunction with the accompanying drawings of which.

BEST MODE FOR CARRYING OUT THE INVENTION

Hereinafter, example embodiments will be described in detail with reference to the accompanying drawings. It should be understood, however, that there is no intent to limit this disclosure to the particular example embodiments disclosed. On the contrary, example embodiments are to cover all modifications, equivalents, and alternatives falling within the scope of the example embodiments.

The terminology used herein is for the purpose of describing particular example embodiments only and is not intended to be limiting. Terms such as first, second, A, B, (a), (b), and the like may be used herein to describe components. Each of these terminologies is not used to define an essence, order, or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component. In addition, it should be noted that if it is described in the specification that one component is "directly connected" or "directly joined" to another component, a third component may not be present therebetween.

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings.

Figure 1:
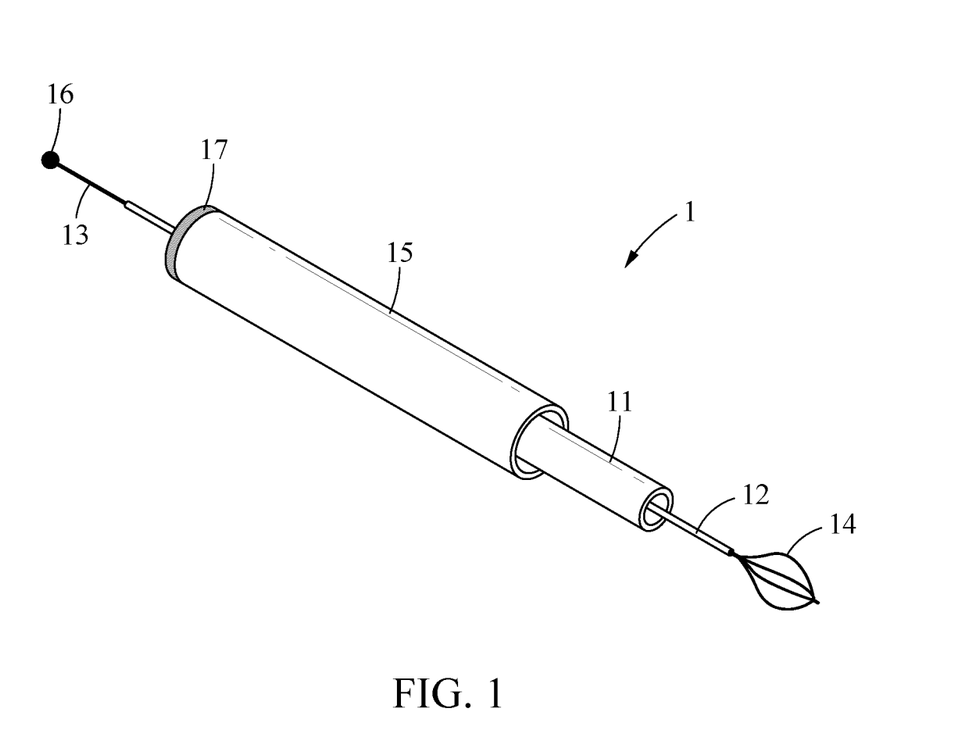
FIG. 1 is a perspective view of an example of a urolithiasis removing device according to an example embodiment.
Figure 2:
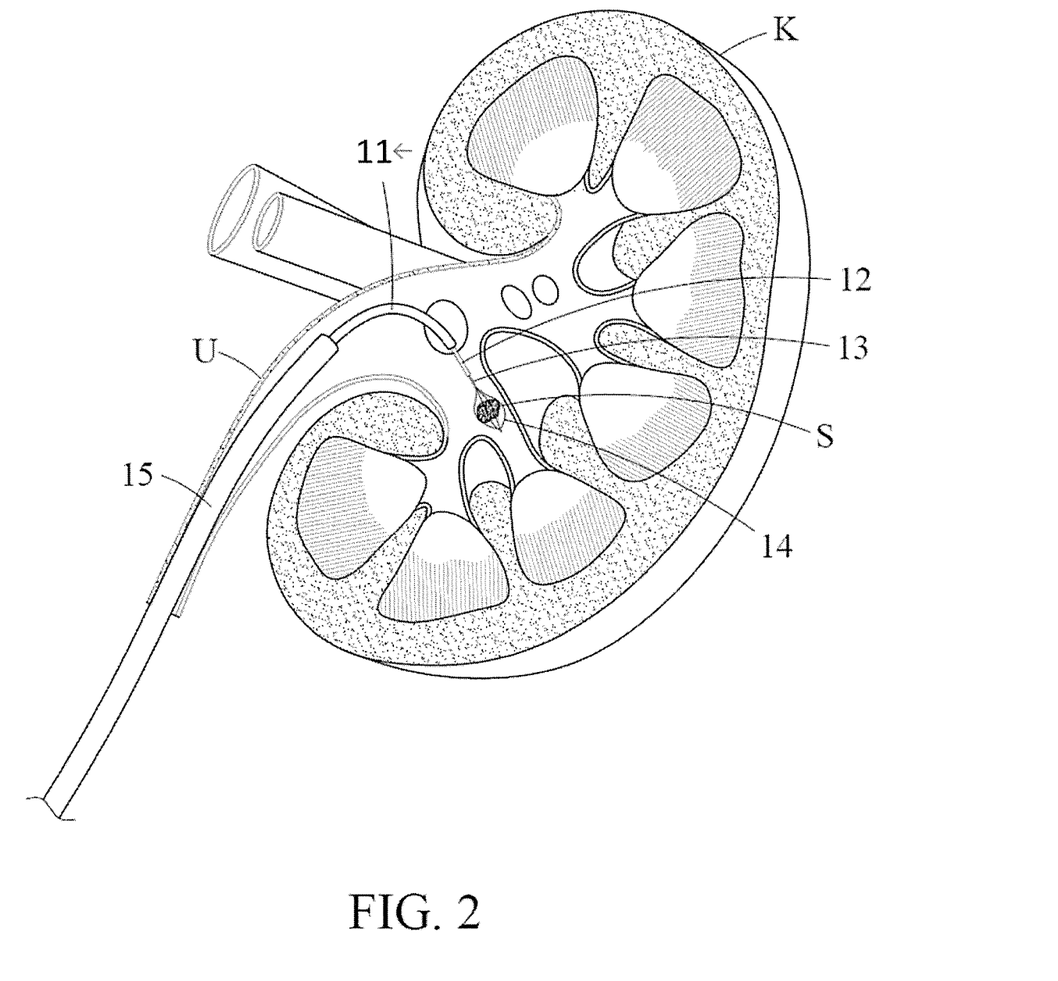
FIG. 2 is a diagram illustrating an example of how a urolithiasis removing device removes a stone from the inside of a body according to an example embodiment.
Figure 3:
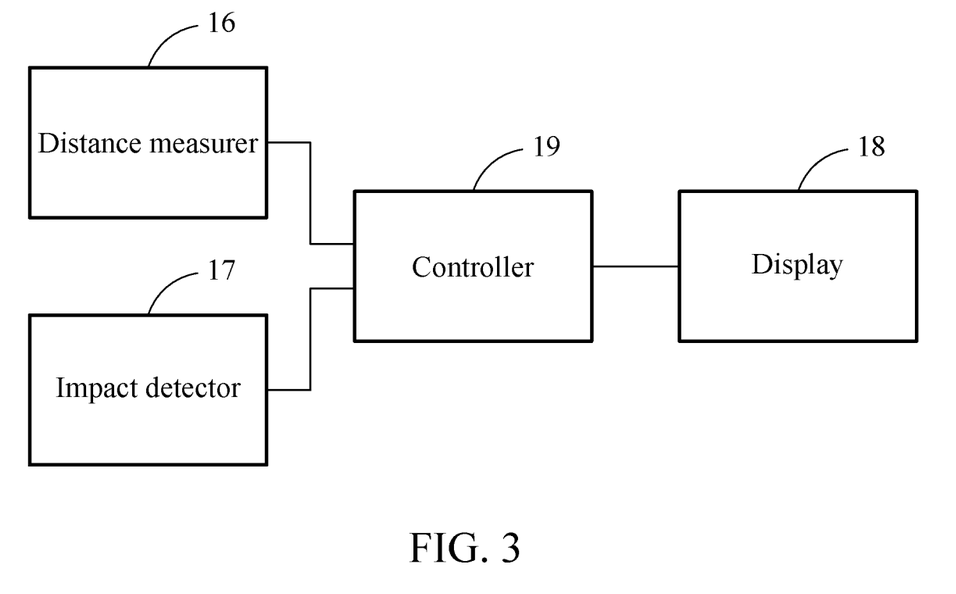
FIG. 3 is a diagram illustrating an example of a configuration of a urolithiasis removing device according to an example embodiment.

FIG. 1 is a perspective view of an example of a urolithiasis removing device according to an example embodiment. FIG. 2 is a diagram illustrating an example of how a urolithiasis removing device removes a stone from the inside of a body according to an example embodiment. FIG. 3 is a diagram illustrating an example of a configuration of a urolithiasis removing device according to an example embodiment.

A urolithiasis removing device 1 may measure a size of a urolithiasis or a stone (hereinafter referred to as only stone), and identify a stone with a size greater than a ureter. The urolithiasis removing device 1 may measure the size of the stone at a position near the stone, without a need to take the stone out of a kidney K. The urolithiasis removing device 1 includes an insertion tube 11, a guide 12, a wire 13, a basket 14, a sheath 15, a distance measurer 16, an impact detector 17, a controller 19, and a display 18. The urolithiasis removing device 1 may determine a size of a stone S based on a pushing distance by which the basket 14 is pushed with respect to the guide 12, at a position near a position at which the stone S is held or grabbed by the basket 14. In addition, after moving the guide 12, the wire 13, and the basket 14 toward the insertion tube 11 while the stone S is being held by the basket 14, and when the basket 14 is caught on the insertion tube 11, the urolithiasis removing device 1 may measure a relative position of the wire 13 with respect to the insertion tube 11 and determine the size of the stone S based on the measured relative position.

The urolithiasis removing device 1 may perform each of the following three relative movements. Firstly, in a state in which the sheath 15 is in a ureter U, the insertion tube 11 is relatively movable with respect to the sheath 15. Secondly, the guide 12 is relatively movable with respect to the insertion tube 11. Thirdly, the wire 13 is relatively movable with respect to the guide 12. The basket 14 may include a material, for example, a shape-memory alloy, which is configured to restore an initial shape exhibited when an external force is not applied. The basket 14 may move forward or backward by the wire 13, and may change its state to an expanded state in which an external force is not applied and a contracted state in which it is contracted by being pushed by the guide 12. The basket 14 may receive the stone S in an inner side thereof in the expanded state and then be pulled backward to be in the contracted state, and thus stably hold the stone S.

The sheath 15 may be provided inside the ureter U. The sheath 15 may be formed of a rubber material, for example. The sheath 15 may protect an inner wall of the ureter U by preventing the insertion tube 11 and the guide 12 from damaging the inner wall of the ureter U. The sheath 15 may guide a movement of the insertion tube 11. The sheath 15 may have a hollow portion at a center thereof to guide the insertion tube 11.

The insertion tube 11 may be inserted into an inner side of the sheath 15, and relatively movable with respect to the sheath 15. For example, the insertion tube 11 may be construed as being part of an endoscope, and an end thereof may be bent according to an operation of the endoscope, thereby moving toward a position where a stone is present. The insertion tube 11 may have a hollow portion at a center thereof to guide the guide 12.

The guide 12 may be inserted into an inner side of the insertion tube 11, and relatively movable with respect to the insertion tube 11. The guide 12 may guide the wire 13 and the basket 14 to a position where a stone is present. For example, the guide 12 may be construed as being part of an endoscope, and an end thereof may be bent according to an operation of the endoscope, thereby moving toward a position where a stone is present.

The wire 13 may be inserted into an inner side of the guide 12, and relatively movable with respect to the guide 12. The wire 13 may relatively move backward with respect to the guide 12 until as the basket 14 is caught in front of the guide 12 and does not move backward any longer. The controller 19 may determine the size of the stone S based on a relative position of the wire 13 with respect to the guide 12 in a state in which such a relative movement of the wire 13 with respect to the guide 12 is limited by the basket 14. For example, when the size of the stone S is small, the wire 13 may move a relatively greater distance with respect to the guide 12. In contrast, when the size of the stone S is large, the wire 13 may move a relatively less distance with respect to the guide 12.

The basket 14 may be disposed in front of the wire 13 and configured to hold or grab a stone. The basket 14 may hold a stone by changing its state to the expanded state or the contracted state. The basket 14 may include a material, for example, a shape-memory alloy, which is configured to restore an initial shape exhibited when an external force is not applied.

The distance measurer 16 may measure a relative movement distance of the wire 13 with respect to the guide 12. For example, the distance measurer 16 may be provided at a rear end of the wire 13, and configured to measure a distance from the rear end of the wire 13 to the guide 12. The distance measurer 16 may be an infrared sensor or a displacement sensor, for example. The distance measurer 16 may be disposed on an opposite side to the basket 14 based on the guide 12. Such a structure may contribute to reducing the number of components provided in front of the guide 12, and it is thus possible to compactly embody a front portion of the urolithiasis removing device 1, for example, an area of the basket 14. The distance measurer 16 may transmit displacement information of the wire 13 to the controller 19 which will be described in detail hereinafter.

The impact detector 17 may be provided in the sheath 15 and configured to detect an impact applied to the sheath 15. For example, the impact detector 17 may be a force sensor. For another example, the impact detector 17 may be a strain gauge provided on a side wall of the sheath 15. For example, when the insertion tube 11 moves along an inner side of the sheath 15 while the basket 14 is holding a stone having a diameter greater than an inner diameter of the sheath 15, the basket 14 may collide a front end of the sheath 15, and the impact detector 17 may detect an impact generated by the collision.

The controller 19 may receive a distance information signal measured by the distance measurer 16. The controller 19 may determine a size of a stone based on a relative position of the wire 13 with respect to the guide 12 in a state in which the basket 14 holding the stone is caught on a front end of the guide 12. For example, the controller 19 may determine the size of the stone based on a movement distance of the basket 14 measured by the distance measurer 16. For example, the controller 19 may store therein data in which a relative position of the wire 13 with respect to the guide 12 is matched to a stone size. In addition, the controller 19 may receive an impact signal detected by the impact detector 17. The controller 19 may transmit, to the display 18, stone size information and impact information.

The display 18 may receive the signal from the controller 19 and display the information. A user may verify the stone size information displayed on the display 18, and determine whether to remove a stone. In addition, the user may verify the impact information displayed on the display 18, and determine whether to remove the stone. The impact information may be information as to whether an impact is detected. Here, the occurrence of an impact based on the impact information may indicate that a size of a stone is greater than the inner diameter of the sheath 15. The user may determine whether to remove the stone based on a type of the stone. For example, when the stone has a rough outer surface, the user may reconsider the removal of the stone. However, when the stone has a smooth outer surface, the user may decide to remove the stone along with the sheath 15.

Figure 4:
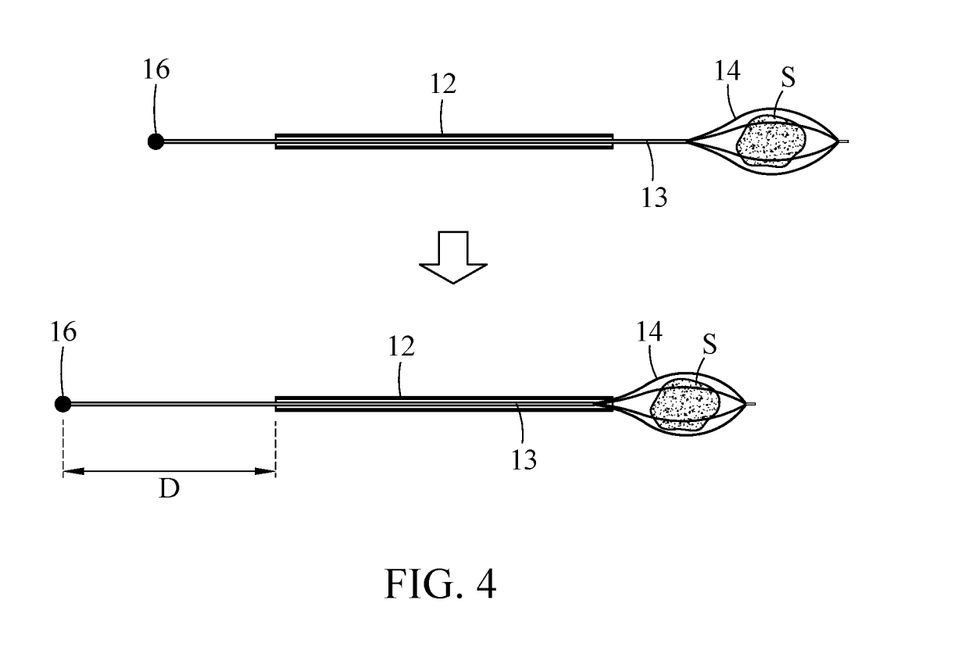
FIG. 4 is a diagram illustrating an example of how a urolithiasis removing device relatively moves a wire with respect to a guide to measure the size of a stone according to an example embodiment.
Figure 5:
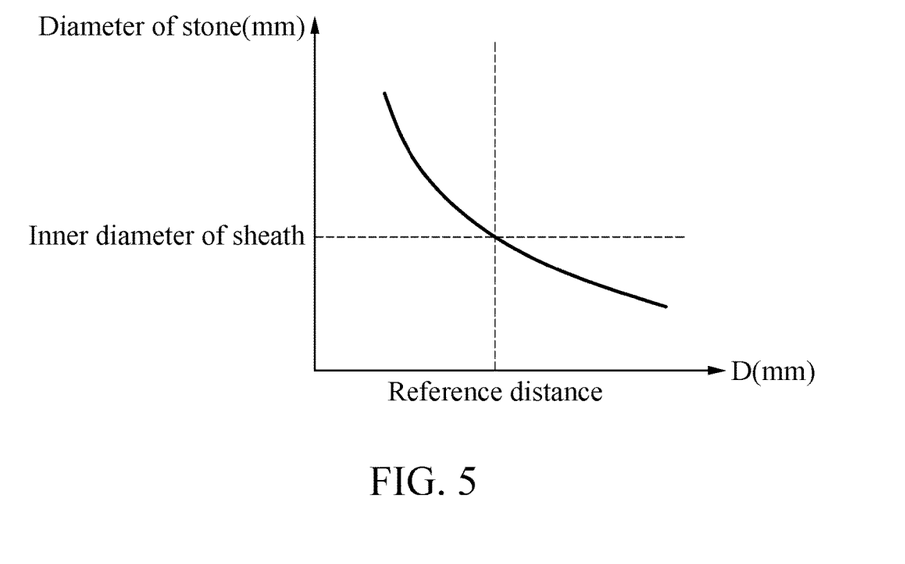
FIG. 5 is a graph illustrating a relationship between a relative position of a wire with respect to a guide and the size of a stone according to an example embodiment.

FIG. 4 is a diagram illustrating an example of how a urolithiasis removing device relatively moves a wire with respect to a guide to measure a size of a stone according to an example embodiment. FIG. 5 is a graph illustrating a relationship between a relative position of a wire with respect to a guide and a size of a stone according to an example embodiment.

In FIGS. 4 and 5, the insertion tube 11 and the sheath 15 are not illustrated.

Referring to FIGS. 4 and 5, when the wire 13 relatively moves forward with respect to the guide 12, the basket 14 may receive a stone S. In such a state, the basket 14 may be in an expanded state. While the basket 14 is holding the stone S inside thereof, the wire 13 may relatively move backward with respect to the guide 12. The basket 14 may move backward by the wire 13, and the basket 14 may be pressed and contracted by a front end of the guide 12. Thus, as the basket 14 changes its state from the expanded state to the contracted state, the basket 14 may more stably support the stone S. The wire 13 may move backward until the basket 14 is not deformed anymore. While the wire 13 is moving, the distance measurer 16 may measure a movement distance of the wire 13 by which the wire 13 moves, and a controller may determine the size of the stone S based on the distance measured by the distance measurer 16.

For example, the distance measurer 16 may be provided at a rear end of the wire 13 and measure a distance D from a current position of the distance measurer 16 to a rear end of the guide 12. The distance measurer 16 may transmit the measured distance D to the controller, and the controller may determine the size of the stone S based on the received distance D. Here, a distance D and a size of a stone S may correspond to each other one-to-one. The controller may store data of a reference distance at which a diameter of the stone S is the same as an inner diameter of a sheath, for example, the sheath 15 illustrated in FIG. 1, and generate an alarm signal when the distance D is less than the reference distance. When the alarm signal is generated, a display, for example, the display 18 illustrated in FIG. 3, and/or a sound alarm device may send the alarm signal to outside.

Figure 6:
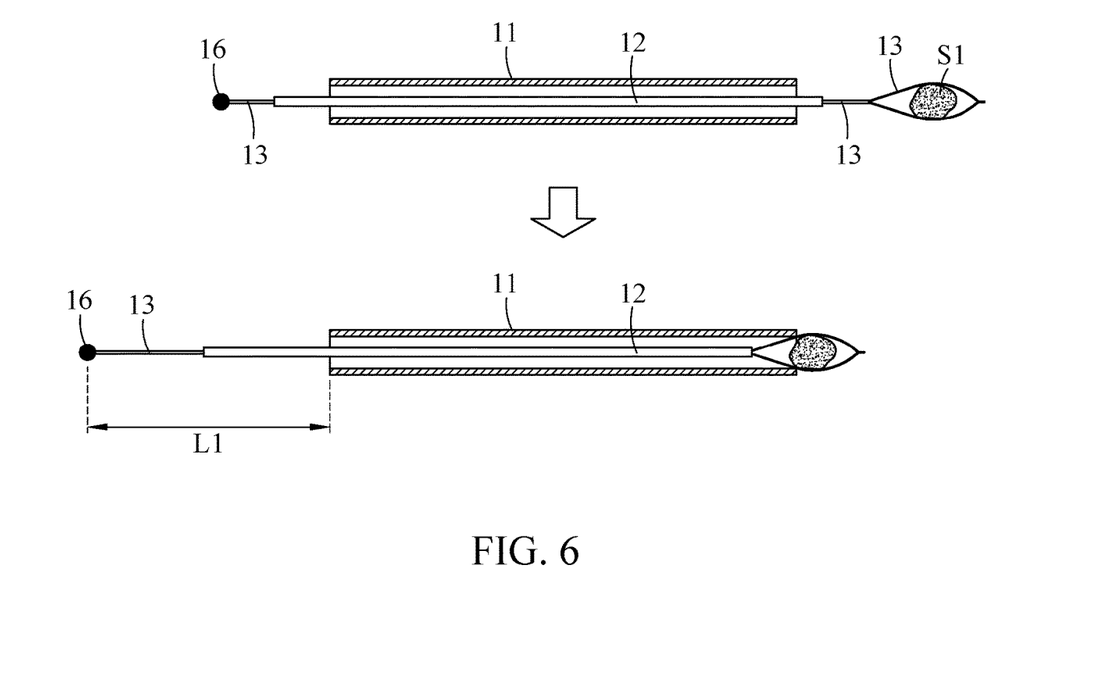
FIG. 6 is a diagram illustrating an example of how a urolithiasis removing device relatively moves a wire and a guide with respect to an insertion tube to measure the size of a stone according to an example embodiment.
Figure 7:
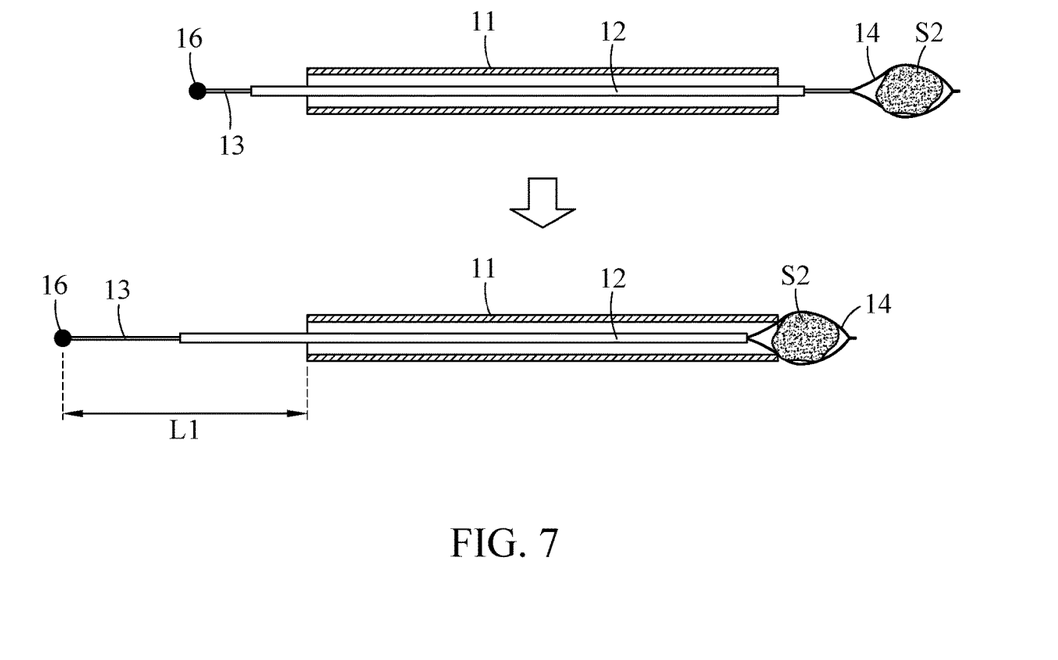
FIG. 7 is a diagram illustrating an example of how a urolithiasis removing device relatively moves a wire and a guide with respect to an insertion tube to measure the size of a stone according to an example embodiment.

FIGS. 6 and 7 are diagrams illustrating an example of how a urolithiasis removing device relatively moves a wire and a guide with respect to an insertion tube to measure a size of a stone according to an example embodiment.

Referring to FIGS. 6 and 7, a user may expand the basket 14 to receive therein a stone S1, and allow the basket 14 to be pressed by the guide 12 and thus be contracted to stably hold or grab the stone S1. An upper portion of FIG. 6 illustrates a state in which the basket 14 is holding or grabbing the stone S1. The basket 14 may be pressed by the guide 12 to the extent that the basket 14 is no longer deformed. Subsequently, the wire 13 and the guide 12 may move together backward. While the wire 13 and the guide 12 are moving backward, the basket 14 may be caught on a front end of the insertion tube 11. A lower portion of FIG. 6 illustrates a state in which the basket 14 is caught on the front end of the insertion tube 11. A controller may determine a size of the stone S1 based on a distance L1 detected by the distance measure 16 in a state in which the basket 14 is caught in the insertion tube 11.

FIG. 7 illustrates a state in which a stone S2 larger than the stone S1 illustrated in FIG. 6 is grabbed. Since a size of the stone S2 in FIG. 7 is relatively larger, a detected distance L2 may be relatively shorter than the detected distance L1 in FIG. 6.

Figure 8:
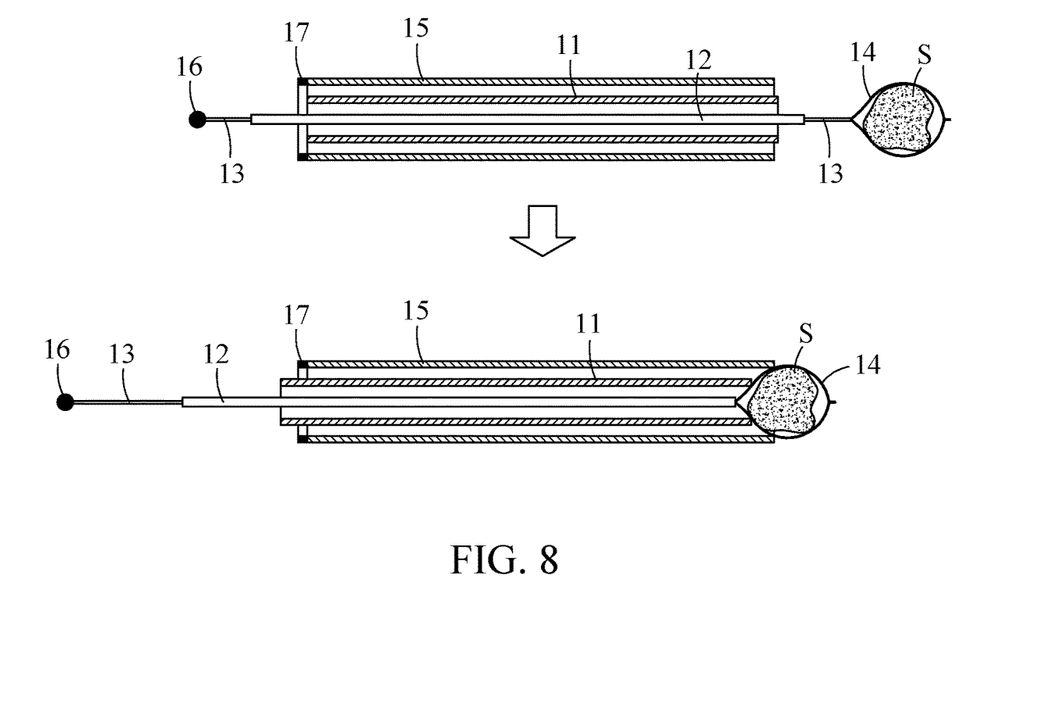
FIG. 8 is a cross sectional view of an example of a urolithiasis removing device according to an example embodiment.

FIG. 8 is a cross sectional view of an example of a urolithiasis removing device according to an example embodiment.

When a size of a stone S is greater than an inner diameter of the sheath 15, the basket 14 which is holding or grabbing the stone S may collide with the sheath 15. When the basket 14 collides with the sheath 15, the impact detector 17 may detect an impact from such a collision and transmit a signal associated with the detected impact to a controller. The controller may display information as to whether the impact is detected or not to outside through a display. Although not illustrated, a urolithiasis removing device may further include an alarm portion. When the impact is detected, the controller may transmit a signal to the alarm portion, and the alarm portion may generate an alarm signal, for example, an alarm.

A user may decide whether to remove the stone S having the size greater than the inner diameter of the sheath 15, based on a type of the stone S. For example, when the stone S has a smooth outer surface, the user may remove the stone S along with the sheath 15.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

The invention claimed is:

1. A urolithiasis removing device comprising:
   an insertion tube;
   a guide configured to be inserted into an inner side of the insertion tube and relatively movable with respect to the insertion tube;
   a wire configured to be inserted into an inner side of the guide and relatively movable with respect to the guide;
   a basket disposed in front of the wire and configured to hold a stone; and
   a controller configured to determine a size of the stone based on a relative movement of the guide with respect to the insertion tube or a relative movement of the wire with respect to the guide
   wherein the controller is configured to determine the size of the stone based on a relative position of the wire with respect to the insertion tube in a state in which the basket holding the stone is caught on a front end of the insertion tube.

2. The urolithiasis removing device of claim 1, further comprising:
   a distance measurer disposed in the wire and configured to measure a relative movement distance of the wire with respect to the guide,
   wherein the controller is configured to determine the relative position of the wire with respect to the insertion tube based on a distance detected by the distance measurer.

3. The urolithiasis removing device of claim 1, further comprising:
   a sheath configured to surround the insertion tube,
   wherein the insertion tube is relatively movable with respect to the sheath.

4. A urolithiasis removing device comprising:
   an insertion tube;
   a guide configured to be inserted into an inner side of the insertion tube and relatively movable with respect to the insertion tube;
   a wire configured to be inserted into an inner side of the guide and relatively movable with respect to the guide;
   a basket disposed in front of the wire and configured to hold a stone;
   a controller configured to determine a size of the stone based on a relative movement of the guide with respect to the insertion tube or a relative movement of the wire with respect to the guide
   a sheath configured to surround the insertion tube, and
   an impact detector provided in the sheath and configured to detect an impact applied to the sheath,
   wherein the insertion tube is relatively movable with respect to the sheath.

5. The urolithiasis removing device of claim 4, further comprising:
   a display configured to display information associated with the size of the stone and information as to whether an impact is detected by the impact detector.

6. A urolithiasis removing device comprising:
   a sheath;
   an insertion tube configured to be inserted into an inner side of the sheath and relatively movable with respect to the sheath;
   a guide configured to be inserted into an inner side of the insertion tube and relatively movable with respect to the insertion tube;
   a wire configured to be inserted into an inner side of the guide and relatively movable with respect to the guide;

a basket disposed in front of the wire and configured to hold a stone; and
a controller configured to determine a size of the stone based on a relative movement of the guide with respect to the insertion tube or a relative movement of the wire with respect to the guide,
a distance measurer disposed in the wire and configured to measure a relative movement distance of the wire with respect to the guide; and
an impact detector provided in the sheath and configured to detect an impact applied to the sheath.

7. The urolithiasis removing device of claim 6, wherein the controller is configured to determine the size of the stone based on a relative position of the wire with respect to the guide in a state in which the basket holding the stone is caught on a front end of the guide.

\* \* \* \* \*